United States Patent [19]
Schuster

[11] 4,057,144
[45] Nov. 8, 1977

[54] HIGH STRENGTH BAG FOR STORING MATERIALS IN STERILE CONDITION

[76] Inventor: Samuel J. Schuster, 1099 Hillside Street, Monterey Park, Calif. 91754

[21] Appl. No.: 635,380

[22] Filed: Nov. 25, 1975

Related U.S. Application Data

[63] Continuation-in-part of Ser. No. 541,720, Jan. 17, 1975, abandoned.

[51] Int. Cl.² .................... A61B 19/02; B65D 33/16
[52] U.S. Cl. ...................................... 206/439; 229/62
[58] Field of Search ................... 206/438, 439, 440; 229/62, 62.5

[56] References Cited

U.S. PATENT DOCUMENTS

| | | | |
|---|---|---|---|
| 2,997,224 | 8/1961 | Stannard | 229/62.5 X |
| 3,370,780 | 2/1968 | Shaw | 229/62.5 |
| 3,394,871 | 7/1968 | Williams et al. | 229/62.5 |
| 3,472,369 | 10/1969 | Schuster | 206/439 |
| 3,761,013 | 9/1973 | Schuster | 206/439 X |

Primary Examiner—Stephen P. Garbe
Attorney, Agent, or Firm—Fraser and Bogucki

[57] ABSTRACT

A flexible bag formed from at least one plastic sheet folded to form a tube and provide overlapping, longitudinally-extending margins, is disclosed. The overlapping margins are joined by a series of longitudinally-spaced bonds, typically heat seals. A membrane permeable to sterilizing vapor and which may comprise a strip of paper having high wet strength is bonded to the tube and overlies the portion of the tube including the overlapping margins. The longitudinally-spaced heat seals preferably secure the overlapping margins to the membrane as well. The various heat seal patterns for joining the overlapping margins and membrane, as well as particular embodiments of the bag for retaining liquid and dry contents, are also disclosed. The sealing arrangement of the invention provides a bag capable of holding, even under autoclaving conditions, bulky, heavy materials which would otherwise rupture the paper strip or the seals joining the strip to the plastic tube.

28 Claims, 21 Drawing Figures

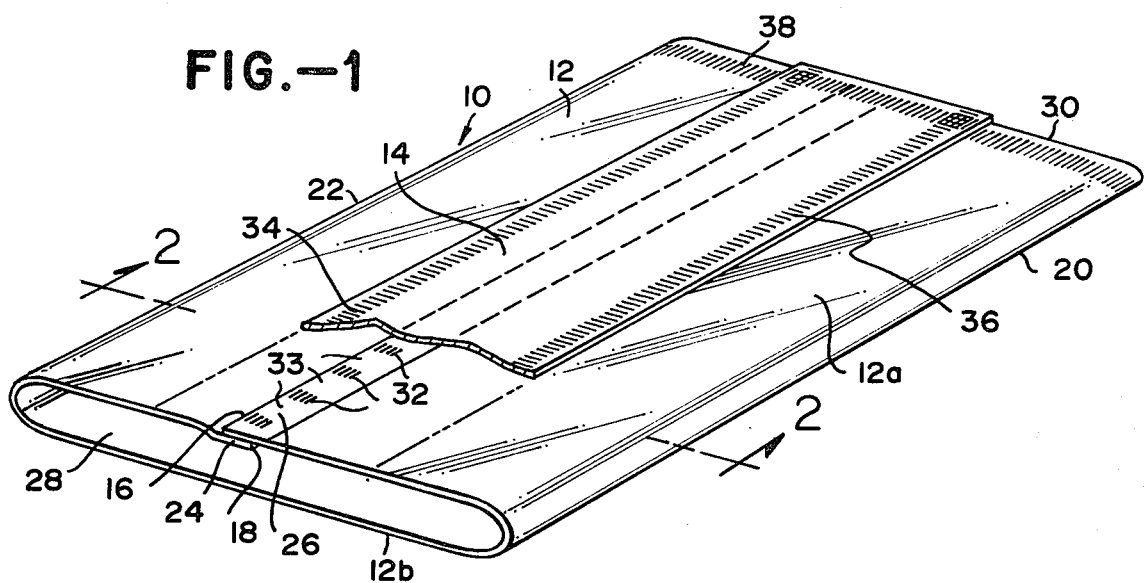
FIG.-1
FIG.-2
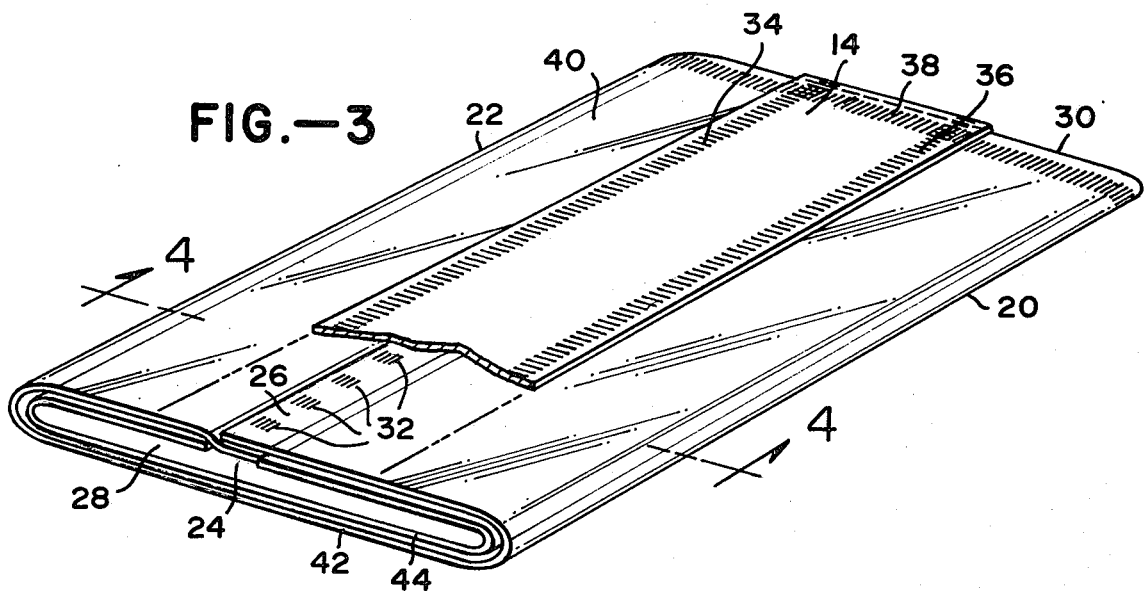
FIG.-3
FIG.-4

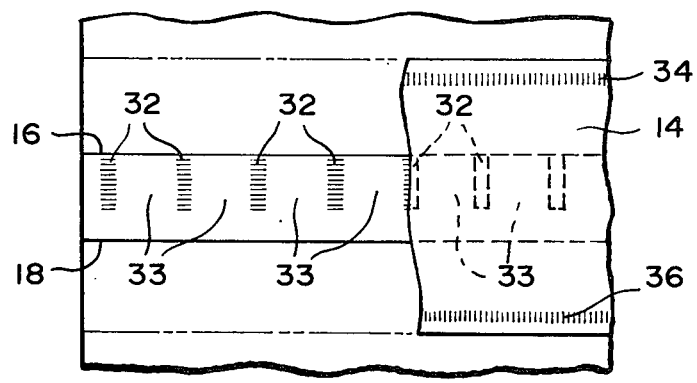
FIG.—5
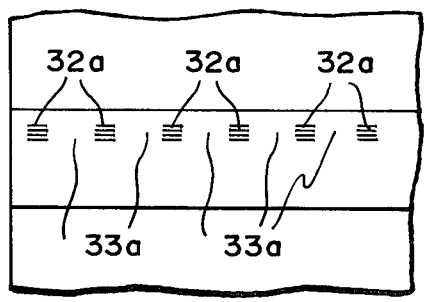
FIG.—6
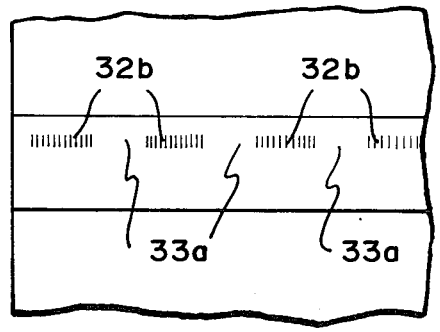
FIG.—7
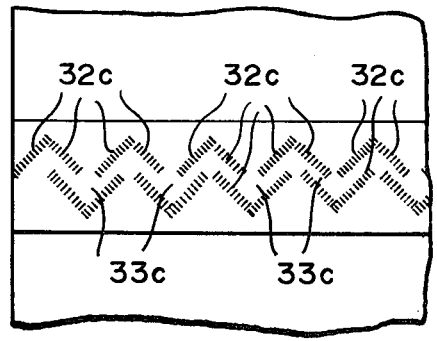
FIG.—8

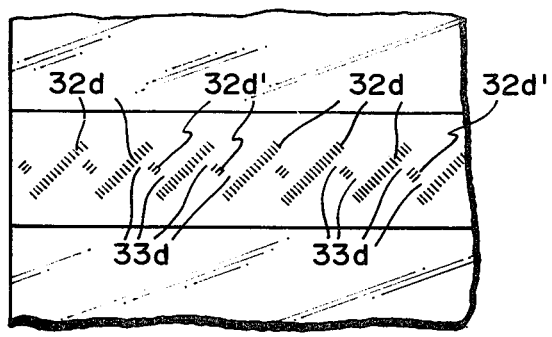
FIG.—9
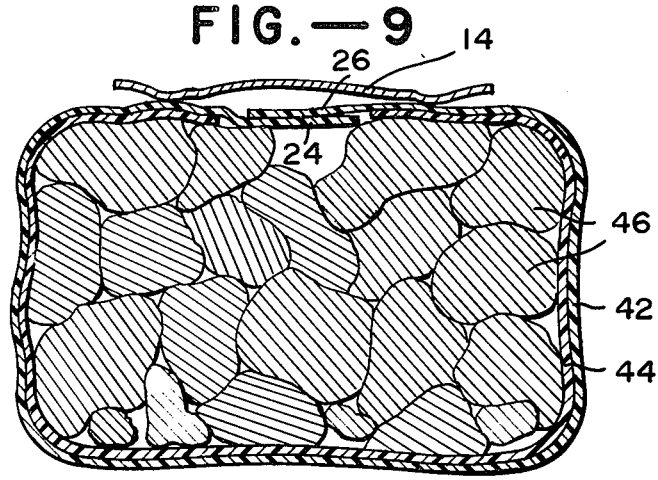
FIG.—10
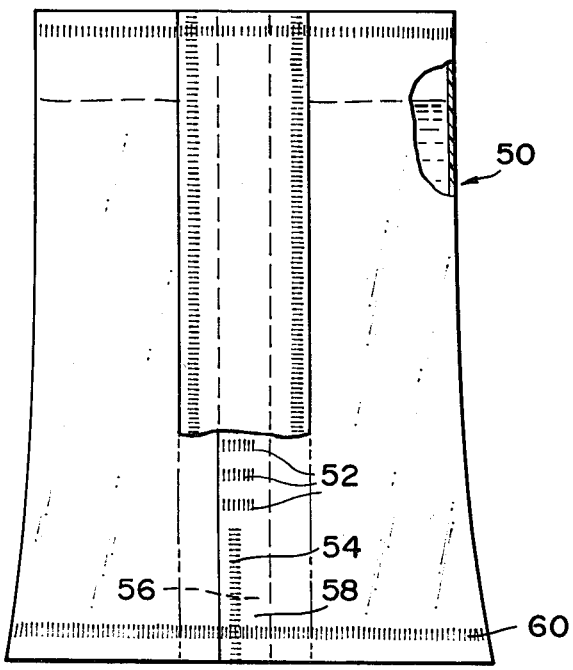
FIG.—11

HIGH STRENGTH BAG FOR STORING MATERIALS IN STERILE CONDITION

RELATED APPLICATIONS AND PATENTS

This application is a continuation-in-part of application Ser. No. 541,720, filed Jan. 17, 1975, now abandoned, and entitled "High Strength Bag For Storing Materials in Sterile Condition".

Application Ser. No. 236,409, filed Mar. 20, 1972, for "Double Wall Package for Storing Items in Bacteria-Free Condition", now U.S. Pat. No. 3,761,013 issued Sept. 25, 1973 and application Ser. No. 648,310, filed June 23, 1967 for "Readily Opened Package for Storing Items in Bacteria-Free Condition", now U.S. Pat. No. 3,472,369 issued Oct. 14, 1969, are incorporated herein by reference for background purposes and for their disclosures of certain relevant structural features.

BACKGROUND OF THE INVENTION

1. Field of the Invention

The present invention relates generally to improved bag structures and particularly to high strength bags capable of retaining bulky, relatively heavy materials in sterile condition and whose strength is essentially unaffected even when subjected to steam sterilization.

2. History of the Prior Art

Various bags have been developed for retaining articles which are sterilized after being packaged. Such bags typically comprise a composite structure consisting of plastic sheet material and a membrane permeable to sterilizing vapors such as ethylene oxide or steam. For example, the above-referenced U.S. Pat. Nos. 3,472,369 and 3,761,013 disclose bags consisting generally of plastic sheet folded along longitudinal fold lines to define a longitudinal opening. The opening is covered by a readily removable, vapor-permeable closure membrane typically in the form of a paper strip. It has been found that when such bags are made large enough to hold bulky, relatively heavy materials, the stresses developed when the bag is filled may result in rupturing of the seals joining the plastic sheet material and paper membrane. This problem is aggravated when the filled bag is subjected to autoclaving, that is, steam sterilization, which by itself has the effect of weakening the paper membrane.

There is furthermore a present need for an autoclavable, flexible container or bag capable of retaining large amounts of hospital waste products which typically include a large percentage of liquid and semi-liquid masses. Such a need has arisen from the recent enactment of anti-pollution ordinances in certain areas which prohibit the incineration by hospitals of waste products, Such ordinances require waste products to be sterilized by autoclaving and then disposed of in the same manner as other refuse. Such waste products may include, besides the aforementioned liquid and semi-liquid surgical waste, disposable surgical instruments and apparel, bandages, sutures and petri dishes.

Currently, the aforementioned waste products are simply wrapped in paper or cloth and in this fashion subjected to the autoclaving process. Such improvised containers, however, often do not adequately retain their contents, particularly those in the liquid or semi-liquid state. Paper, especially, is prone to leakage and moreover, as stated, loses much of its strength when exposed to the autoclaving process.

SUMMARY OF THE INVENTION

Bags according to the present invention are constructed to have superior strength to retain bulky, relatively heavy material in sterile condition. Moreover, their ability to retain such materials, including hospital waste products having a liquid or semi-liquid composition, is virtually unaffected by exposure to autoclaving temperature and moisture conditions.

Pursuant to one particular embodiment of the present invention, there is provided a high strength, autoclavable bag comprising an envelope or tube made of at least one ply of sheet plastic essentially impermeable to bacteria and having overlapping margins joined by a series of spaced heat seals defining between them passages through which the sterilizing vapor can easily pass during a sterilizing cycle. Covering a portion of the plastic tube, such portion including the overlapping margins, is a membrane that is highly permeable to sterilizing vapor in comparison to the plastic tube, while being essentially impermeable to bacteria. The membrane is joined to the tube by continuous heat seal joinder lines paralleling the overlapping margins. The bag further has an open end for receiving the materials to be sterilized.

To stabilize the position of the overlapping margins relative to the membrane, provide further protection of the membrane from damage and facilitate manufacture of the bag, the membrane is preferably, secured to the overlapping margins by the mentioned series of spaced heat seals.

Following loading of the bag, the open end is heat sealed and the filled bag is subjected to the sterilizing cycle. During this cycle sterilizing vapor enters the interior of the bag through the membrane and through the passages between the overlapping margins of the envelope to sterilize the contents. If the autoclaving process is used, the steam causes saturation and some weakening of the membrane which typically takes the form of a paper strip. However, since the stresses on the bag causes by the weight of the contents are carried by the series of heat seals bridging the overlapping margins of the plastic tube rather than by the membrane, there is no tendency for the membrane to tear or rupture. Moreover, when the contents include semi-liquid or liquid matter, leakage is prevented by virtue of the overlapped margins which tend to be intimately pressed together as a result of the outwardly-directed pressure of the content.

The heat seals joining the overlapping margins of the tube may be applied in a variety of patterns. In accordance with alternative forms of the invention, such heat seals may be angularly oriented or V-shaped to define sterilizing vapor passages of a labyrinthine nature which impose more of a barrier to the escape of the enclosed materials yet still permit the vapor to readily enter the interior of the bag.

In still another form of the invention, the plastic tube may comprise a double wall or two ply structure in which the overlapping margins are interleaved in such fashion that substantially all cross sections of the tube have substantially the same, uniform thickness. Such construction, described in greater detail in the above-referenced U.S. Pat. No. 3,761,013, not only increases the strength of the bag and renders it more resistant to the effects of abrading, but facilitates its fabrication of high temperature plastics, such as polypropylene, capable of withstanding autoclaving temperatures.

The overlapping margins may also be joined by a continuous bond or heat seal extending along a portion of the length of the bag from the initially closed end thereof. In this way, added strength and resistance to leakage is furnished at the bottom of the bag where the greatest stress exists when the bag is filled with liquid or semi-liquid material. Such a continuous, longitudinally oriented bond need only extend a short distance from the bottom of the bag and in most instances will be substantially less than half the overall length of the bag.

In another example of the invention, particularly suitable for retaining dry waste materials, each margin of the plastic tube may be provided with notches so as to define along the margin a series of projecting tabs. The tabs of one of the margins are bonded to the corresponding tabs of the other margin and sterilizing vapor readily enters the bag through the overlying membrane and the openings between adjacent pairs of tabs.

BRIEF DESCRIPTION OF THE DRAWINGS

Other objects, advantages and features of the invention will be understood by reference to the following detailed description, taken in conjunction with the accompanying drawings, in which:

FIG. 1 is a partially broken away, perspective view of a bag according to one embodiment of the invention;

FIG. 2 is a transverse cross section of the bag of FIG. 1 as taken along the line 2—2;

FIG. 3 is a partially broken away, perspective view of a bag according to another embodiment of the invention;

FIG. 4 is a transverse cross section of the bag of FIG. 3 as taken along the line 4—4;

FIG. 5 shows a portion of a bag in accordance with either of the embodiments of FIGS. 1—4 detailing the heat seal pattern employed at the overlapping margins;

FIG. 6–9 show various alternative heat seal patterns that may be applied to the overlapping margins of bags according to the invention;

FIG. 10 is a transverse cross section of the bag of FIGS. 3 and 4 as it would appear when filled with material to be sterilized;

FIG. 11 is a side view of another form of bags according to the invention which is particularly suitable for containing liquid and semi-liquid materials;

DETAILED DESCRIPTION OF THE PREFERRED EMBODIMENTS

Figure 12:
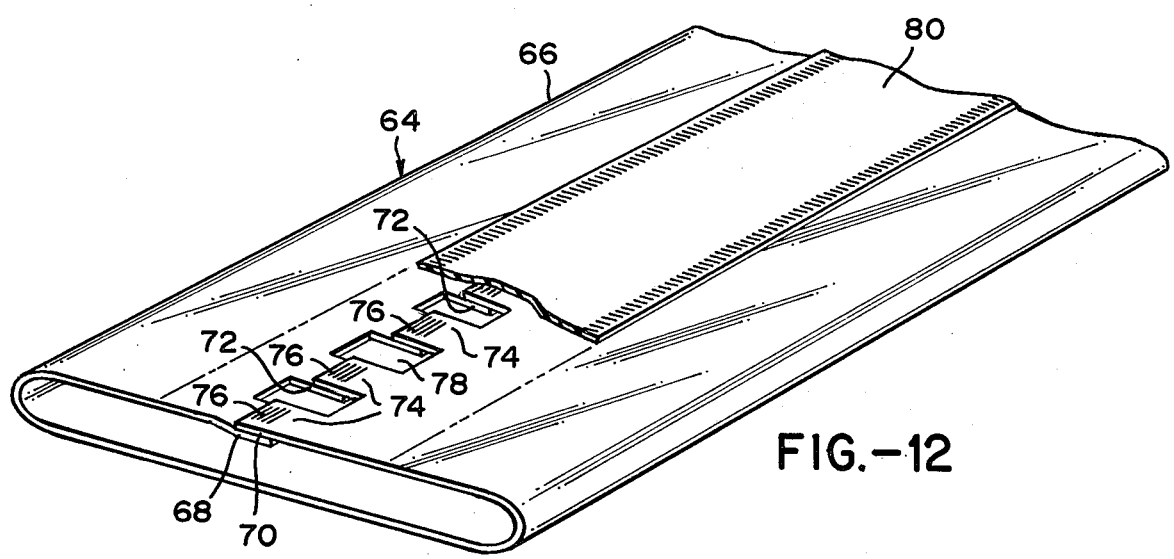
FIG. 12 is a partly broken away, perspective view of still another example of bags according to the invention that is useful for holding dry materials to be sterilized.

At the outset it should be noted that in the accompanying drawings the thicknesses of the sheet materials forming the bags have all been greatly exaggerated in order to clearly show their interrelationship. Further, it will be evident that a great many combinations of materials, overall package dimensions, material properties, specific package configurations, and so forth, fall within the purview of the claimed invention; only relatively few specific examples are shown and discussed herein and these should not be construed as exhaustive.

Referring to FIGS. 1 and 2, there is shown a bag 10 according to one embodiment of the invention. The bag 10 comprises basically a flexible plastic container or tube 12 and an elongated membrane 14. The tube 12 is preferably made of a single sheet of heat-sealable plastic such as high density polyethylene, polypropylene, mixtures of polyethylene and polypropylene, nylon, polybutylene or the like. To withstand the temperature levels typically employed in autoclaves, it is necessary to use "high temperature" plastics such as the above, but it will be evident that bags of the invention may also be used with sterilizing vapors such as ethylene oxide in which case lower temperature plastics such as low density polyethylene may be employed.

The thickness of the material constituting the tube 12 is sufficient to withstand handling, provide the tube with adequate strength to retain the contents to be sterilized and form an effective barrier to the transmission of bacteria. For typical applications, relatively heavy gauge plastic sheets having a thickness of the order of 3 or 4 mils, for example, will be sufficient to comply with the requirements of strength and handling.

The tube 12 is fabricated from a single, continuous plastic sheet, the longitudinal side edges 16 and 18 of which are folded inwardly along parallel, longitudinal fold lines 20 and 22 to define opposed faces 12a and 12b. The tube further has overlapping longitudinal margins 24 and 26 adjacent the edges 16 and 18, and transverse ends 28 and 30.

The overlapping margins 24 and 26 in accordance with an aspect of the invention are joined by a series of spaced bonds 32 preferably in the form of heat seals which between them define a series of passages 33. In the embodiment under discussion, and in this connection reference is also made to FIG. 5 of the drawings, the heat seals 32 and intervening passages 33 extend in a transverse direction, the lengths of the heat seals 32 being substantially greater than their widths. In one typical, specific example of the invention, the tube 12 when laid flat is about six inches wide between longitudinal folds 20 and 22 and eighteen inches long and the heat seals 32 joining the overlapping longitudinal margins have a width of about 3/32 inch, a length of about ⅜ inch and are spaced apart about ⅜ inch center to center.

Other heat seal arrangements are shown in FIGS. 6 and 7. In FIG. 6 small, generally square heat seals 32a, typically 1/16 inch to 3/32 inch on a side, unite the overlapping margins and define passages 33a, In FIG. 7, elongated heat seals 32b extending in a longitudinal direction parallel to the longitudinal edges of the tube provide increased strength over the configuration employed in FIG. 6. Passages 33b are defined by the heat seals 32b.

The membrane 14 comprises a longitudinal strip somewhat wider than the width of the overlapping margins 24 and 26. The membrane functions as a barrier to bacteria yet is highly permeable to sterilizing vapor and may be made of a strip of conventional paper 3 to 7 mils thick. Preferably, a low porosity, long fiber paper having superior wet strength may be used so that the membrane will remain intact if autoclaving is used. Alternatively, paperlike materials such as "Tyvek", a spun polyolefin of the duPont Company, may be used.

The membrane 14 and the tube 12 are bonded together along longitudinal joinder lines 34 and 36. The bonds are preferably and most easily obtained by heat sealing using spaced-apart heat sealer bars elevated to the required heat sealing temperature. The bonding may also be provided by adhesive or other forms of chemical or mechanical bonding. In the examples shown in the drawings, the membrane 14 is centrally disposed, that is, approximately equidistant from each of the fold lines 20 and 22. It will be evident, however, that the tube 12 can be fabricated so that the overlapping margins 24 and 26 are closer to one fold line or the other with the membrane 14 asymmetrically disposed accordingly.

The membrane 14 can also be provided with a thin polyethylene coating (not shown), such coating being in contact with the outer surface of the tube 12, to facilitate heat sealing the membrane and tube. The thickness of the polyethylene coating is preferably of the order of ¼ mil which is insufficient to impede the passage of sterilizing vapor but nevertheless of sufficient thickness to provide an adequate heat seal joinder. Alternatively, direct heat sealing of the membrane 14 and the tube 12 is made possible by treating the seal areas of the tube with a corona discharge produced, for example, by a voltage of about 10–30 kv at a frequency of 3–5 kHz.

One of the transverse ends 30 of the tube 12 is closed by means of a transverse joinder line 38 which unites the front and rear faces of the bag 10 and the membrane 14. The joinder line 38 is also preferably and most conveniently produced by heat sealing. The other end 28 is open to receive the material to be sterilized.

Turning now to FIGS. 3 and 4, another embodiment of the invention is shown similar in all respects to the embodiment of FIGS. 1 and 2 except that the former utilizes a tube 40 formed of two plies—an outer ply 42 and an inner ply 44—instead of a single ply. All of the remaining elements are identical to those of FIGS. 1 and 2 and are designated by like reference numerals. The construction of bags according to FIGS. 3 and 4 is along the lines disclosed in the above-referenced U.S. Pat. No. 3,761,013 and as explained in that patent has the advantage of permitting use of high temperature materials such as polypropylene while eliminating problems of burn-throughs and singeing of the membrane 14 during the application of the transverse heat seals. In this connection, as pointed out in greater detail in said patent, the total thickness of the plies 42 and 44 of the tube 40 is substantially the same along substantially all cross sections and avoids any difficulties encountered with configurations such as those in which the central portion of the bag is thicker than the other portions. The reduction of such differential thicknesses afforded by the embodiment of FIGS. 3 and 4 greatly facilitates the fabrication of bags using high temperature plastics by eliminating the need for close temperature control or differential heating of the heat sealing bars.

In use, the bag of the invention is filled with the material to be sterilized and the open end 28 is sealed by means of a transverse heat seal such as that already applied to the closed end 30. By way of example, FIG. 10 shows, in cross section, a bag in accordance with FIGS. 3 and 4 after it has been filled. In the absence of the multiple heat seals 32 joining the overlapping margins 24 and 26, the bulk and weight of the material 46 in the bag of FIG. 10 might cause the membrane and/or the heat seals joining the membrane and the plastic to rupture allowing material 46 to escape. In accordance with the invention, the stresses produced by the weight of the contents is carried by the heat seals across the overlapping margins and consequently, there is no stress on the membrane. Moreover, although sterilizing vapor can flow through the passages 33, the outwardly directed pressure produced by the contents of the bag tends to press together the overlapping margins to effectively seal the materials inside and prevent leakage thereof. This advantage provided by the overlapping margins may be considerably enhanced by using heat seal patterns of the type shown in FIGS. 8 and 9.

In FIG. 8, a double row of spaced, V-shaped heat seals 32c is employed. The overlapping or nested nature of the V-shaped seals defines labyrinth passages 33c which, although not impeding the flow of sterilizing vapor between the exterior and interior of the bag, effectively trap the materials inside the bag. More than two rows of such seals may, of course, be used. A somewhat similar arrangement is shown in FIG. 9. Angularly oriented long and short heat seals 32d and 31d', respectively, are alternated along the length of the overlapping margins. The spaces 33d between adjacent heat seals permit the entry and egress of the sterilizing vapor but again, the outwardly directed pressure of the contents of the bag prevent leakage.

Turning now to FIG. 11, there is shown another embodiment of the present invention in the form of a bag 50 particularly suitable for the containment of liquid and semi-liquid masses. The bag 50 may be similar tin all respects to those shown in FIGS. 1 or 3 and may employ any of the described heat seal patterns for uniting the overlapping margins. By way of example, transversely extending, elongated heat seals 52 are shown of the type already described in connection with FIGS. 1, 3 and 5. The embodiment of FIG. 11 differs in that there is provided a continuous, longitudinal joinder line 54, preferably a heat seal, bonding the overlapping margins 56, 58 and extending from the lower extremity of the bag, across the transverse end seal 60 and up along a portion of the length of the bag. This continuous heat seal 54 precludes any leakage of liquid or semi-liquid contents due to the higher pressure which would exist in the lower part of the bag.

Another bag 64 according to the invention is shown in FIG. 12. This embodiment is designed especially for the retention of dry materials. The bag 64 includes a plastic tube 66, as already described, having longitudinal, overlapping margins 68 and 70 that are serrated or notched to form tabs 72 and 74, respectively, which are held together by heat seals 76. Adjacent overlapping tabs are separated by openings 78 through which the sterilizing vapor is free to pass. Little or no restriction is thereby introduced to the flow of vapor in and out of the bag while the bonded tabs 72, 74 provide the required strength to keep the tube 66 intact and prevent rupturing of the overlying membrane 80 or the heat seals joining the membrane 80 and plastic tube 66.

Figure 13:
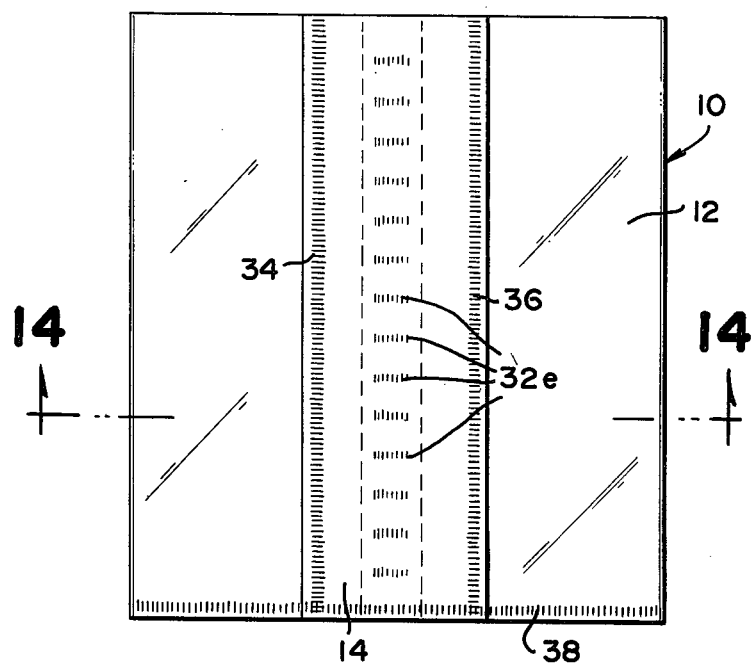
FIG. 13 is a side view of another form of the bags according to the invention.
Figure 14:
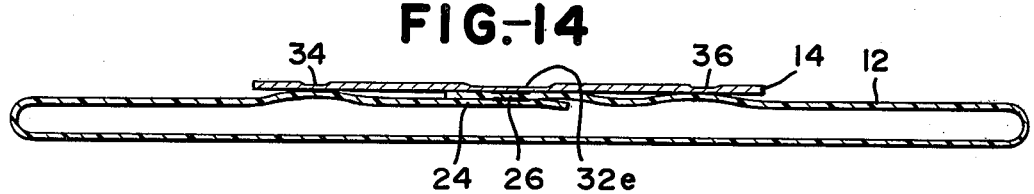
FIG. 14 is a transverse cross section of the bag of FIG. 13 as taken along the line 14—14.

The longitudinally-spaced heat seals preferably are applied to pass through the membrane 14 and the overlapping margins 24, 26 so that the membrane 14 is secured to the overlapping margins along their entire lengths. Besides stabilizing the position of the overlapping margins, such construction helps prevent damage to the membrane and facilitates manufacture. FIGS. 13 and 14 accordingly shows a bag 10 similar to that shown, for example, in FIGS. 1 and 2. The membrane 14 is joined to the overlapping margins 24 and 26 by longitudinally-spaced heat seals 32e which in the embodiment shown have transversely-extending, generally rectangular configurations, but which may take the alternate forms shown, for example, in FIGS. 6-9, as will be described in greater detail below. A supplemental strengthening seal as well as an overlapping tab configuration, such as those shown in FIGS. 11 and 12, respectively, may also be employed.

Figure 15:
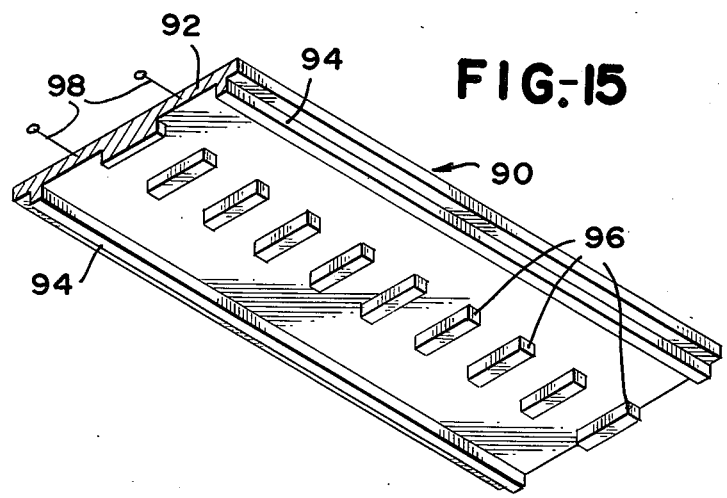
FIG. 15 is a perspective view of a heat sealing device that may be used for fabricating the bag of FIGS. 13 and 14; and, FIGS. 16–21 show portions of various embodiments of bags of the type of FIGS. 13 and 14 and detail various heat seal patterns.

The longitudinally-spaced heat seals 32e in FIG. 13 and 14 are preferably formed simultaneously with the continuous longitudinal seals 34 and 36 and FIG. 15 shows a heat sealer 90 for accomplishing such simultaneous sealing. Heat sealer 90 includes a base 92 supporting longitudinal heat seal bars 94, for applying the seals 34, 36, and spaced heat seal bars 96 for applying the seals 32e. Heater wires 98 extend from one end of the base 92.

Figure 16:
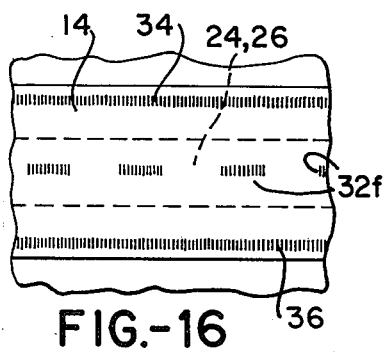
Figure 17:
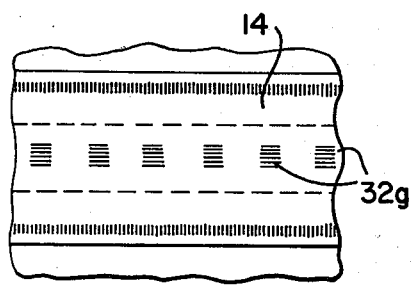
Figure 18:
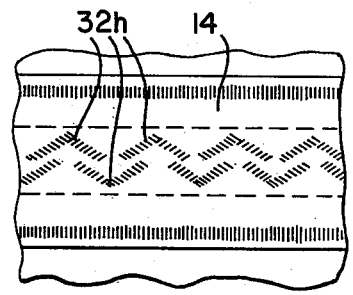
Figure 19:
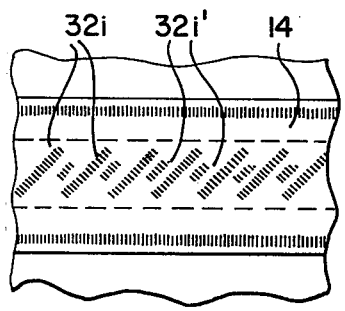

FIGS. 16–19 show various seal configurations generally of the same shapes as those previously described in connection with FIGS. 6–9. In the cases of FIGS. 16–19, the longitudinally-spaced heat seals pass through both the overlapping margins 24, 26 and the membrane 14. Thus, FIG. 16 shows longitudinally oriented, rectangular, spaced seals 32f; FIG. 17 shows generally square seals 32g; FIG. 18 shows a double row of spaced, V-shaped heat seals 32h and FIG. 19 shows a series of angularly oriented, alternate long and short seals 32i and 32i', respectively.

Figure 20:
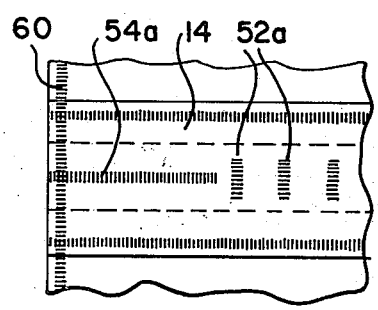

FIG. 20 shows still another embodiment of the present invention in which the longitudinally-spaced heat seals joining the overlapping margins also pass through the membrane 14 and wherein, like the embodiment of FIG. 11, a continuous, longitudinal seal 54a extends from the lower extremity of the bag along a portion of the length of the bag. Longitudinally-spaced, transverse heat seals 52a are of the configuration already described in connection with FIG. 11 but may, of course, assume any of the various configurations already described.

Figure 21:
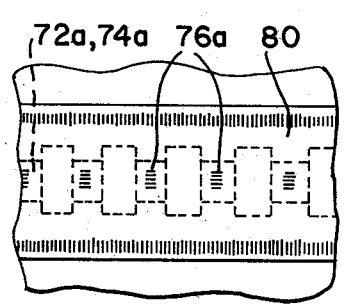

FIG. 21 shows a portion of a bag similar to that shown in FIG. 12 and in which the membrane 80 and overlapping tabs 72a and 74a are joined by longitudinally-spaced heat seals 76a.

What is claimed is:

1. A high strength, bacteria-impermeable, sealable bag for receiving material for sterilization after sealing of the bag by a process employing a sterilizing vapor, the bag comprising:
    a container former of plastic sheet and having opposed faces and opposed transverse ends, one of the faces including overlapping longitudinal margins, the other face being continuous, the longitudinal margins being joined by a plurality of longitudinally-spaced heat seals defining between them passages for the sterilizing vapor; and
    a membrane covering the longitudinal margins and passages and bonded to the container by continuous, longitudinally-extending heat seal joinder lines, the membrane being highly permeable to the sterilizing vapor, a transverse heat seal joinder line adjacent one of the transverse ends uniting the membrane and the container and closing one end of the bag, the other end being open to receive the material to be sterilized, the membrane being secured to the overlapping margins by the longitudinally-spaced heat seals.

2. A bag, as defined in claim 1, in which the longitudinally-spaced heat seals comprise a series of transversely-extending heat seals.

3. A bag, as defined in claim 1, in which the longitudinally-spaced heat seals comprise a series of longitudinally-extending heat seals.

4. A bag, as defined in claim 1, in which the longitudinally-spaced heat seals include sets of heat seals oriented angularly the respect to the longitudinal and transverse directions to define labyrinthine passages.

5. A bag, as defined in claim 1, in which the margins are joined by a continuous longitudinal heat seal extending from the closed end of the bag along a portion of the overall length of the bag.

6. A bag, as defined in claim 1, in which each longitudinal margin is shaped to define a series of longitudinally-spaced tabs, the tabs of one of the margins being heat sealed to the tabs of the other margin by the longitudinally-spaced heat seals.

7. A bag, as defined in claim 1, in which the container is formed of two plies of plastic, substantially all cross sections of the container having substantially the same, uniform thickness.

8. A high strength, sealable, bacteria-impermeable bag for receiving material for sterilization after sealing of the bag by a process employing a sterilizing vapor, the bag including:
    a flexible, bacteria-impermeable plastic container having opposed faces and an open end for receiving the material to be sterilized, one of the faces including overlapping margins of the container, the margins being joined together by a plurality of heat seal bonds spaced along the length of the bag, the bonds defining between them a plurality of passages spaced along the length of the container, the passages providing communication with the interior of the bag for ingress and egress of the sterilizing vapor, the other of the faces being continuous; and
    a membrane impermeable to bacteria but highly permeable, in comparison to the container, to the sterilizing vapor, joined to the container and covering the overlapping margins to prevent the entry of bacteria, the plurality of heat seal bonds securing the membrane to the overlapping margins and carrying stresses produced by the weight of the material received by the bag and relieving the membrane of such stresses.

9. A bag, as defined in claim 8, in which the bonds are shaped and positioned to define labyrinthine passages to impede the entry of bacteria into the interior of the bag.

10. A high strength, sealable, bacteria-impermeable bag for receiving material for sterilization after sealing of the bag by a process employing a sterilizing vapor, the bag including:
    a flexible, bacteria-impermeable plastic container having opposed faces and an open end for receiving the material to be sterilized, one of the faces including overlapping margins of the container, the margins defining between them a plurality of passages spaced along the length of the container, the passages providing communication with the interior of the bag for ingress and egress of the sterilizing vapor, the other of the faces being continuous; and
    a membrane impermeable to bacteria but highly permeable, in comparison to the container, to the sterilizing vapor, joined to the container and covering the overlapping margins to prevent the entry of bacteria, the portions of the plastic container between the passages carrying stresses produced by the weight of the material received by the bag and relieving the membrane of such stresses and in which the end of the container opposite the open end is closed and the one face of the container is devoid of passages along a portion of the length of the bag extending from the closed end.

11. A high strength, bacteria-impermeable, sealable bag for receiving material for sterilization after sealing of the bag by a process employing a sterilizing vapor, the bag comprising:

a flexible tube extending in longitudinal direction and formed of at least one bacteria-impermeable thermoplastic sheet, the tube having opposed ends transverse of the longitudinal direction and overlapping longitudinal margins, the longitudinal margins being joined by a plurality of longitudinally-spaced heat seals defining between them passages providing communication with the interior of the bag for ingress and egress of the sterilizing vapor; and a longitudinally-extending strip covering the longitudinal margins and bonded to the tube by a continuous, longitudinally-extending heat seal adjacent each side of the margins, the strip being impermeable to bacteria but highly permeable, in comparison to the tube, to the sterilizing vapor, a transverse heat seal adjacent one of the transverse ends of the bag uniting the membrane and the tube and closing one end of the bag, the other end being open to receive the material to be sterilized, the longitudinally-spaced heat seals carrying stresses produced by the weight of the material received by the bag and relieving the strip and the heat seals joining the strip and the tube of such stresses and in which the longitudinal margins are joined by a continuous heat seal extending from the closed end of the bag a distance substantially less than half the overall length of the bag.

12. A bag, as defined in claim 11, in which each of the plurality of longitudinally-spaced heat seals has a generally rectangular configuration with the longer side thereof extending along the longitudinal direction of the bag.

13. A bag, as defined in claim 11, in which each of the plurality of longitudinally-spaced heat seals has a generally rectangular configuration with the longer side thereof extending transverse to the longitudinal direction of the bag.

14. A bag, as defined in claim 11, in which each of the plurality of longitudinally-spaced heat seals has a generally square configuration.

15. A bag, as defined in claim 11, in which the plurality of heat seals includes at least two rows of longitudinally-spaced, V-shaped heat seals, the heat seals of adjacent rows being nested to define labyrinthine passages to impede the entry of bacteria into the interior of the bag.

16. A bag, as defined in claim 11, in which the plurality of heat seals extend in directions that are angularly oriented with respect to the longitudinal and transverse directions of the bag.

17. A bag, as defined in claim 16, in which the heat seals are alternately long and short.

18. A bag, as defined in claim 4, in which the longitudinal margins have a plurality of longitudinally-spaced notches defining tabs, the tabs along one of the margins being heat sealed to the tabs along the other margins, the notches defining the passages.

19. A high strength, bacteria-impermeable, sealable bag for receiving material for sterilization after sealing of the bag by a process employing a sterilizing vapor, the bag comprising:

a flexible tube extending in a longitudinal direction and formed of at least one bacteria-inpermeable thermoplastic sheet, the tube having opposed ends transverse of the lingitudinal direction and overlapping longitudinal direction and overlapping longitudinal margins, the longitudinal margins being joined by a plurality of longitudinally-spaced heat seals defining between them passages providing communication with the interior of the bag for ingress and egress of the sterilizing vapor; and a longitudinally-extending strip covering the longitudinal margins and bonded to the tube by a continuous, longitudinally-extending heat seal adjacent each side of the margins, the strip being impermeable to bacteria but highly permeable, in comparison to the tube, to the sterilizing vapor, a transverse heat seal adjacent one of the transverse ends of the bag uniting the membrane and the tube and closing one end of the bag, the other end being open to receive the material to be sterilized, the longitudinally-spaced heat seals carrying stresses produced by the weight of the material received by the bag and relieving the strip and the heat seals joining the strip and the tube of such stresses and in which the plurality of longitudinally spaced heat seals join the strip to the overlapping margins.

20. A high strength, bacteria-impermeable, sealable bag for receiving material for sterilization after sealing of the bag by a process employing a sterilizing vapor, the bag comprising:

a flexible tube extending in a longitudinal direction and formed of at least one bacteria-impermeable thermoplastic sheet, the tube having opposed ends transverse of the longitudinal direction and overlapping longitudinal margins; and a longitudinally-extending strip covering the longitudinal margins and bonded to the tube by a continuous, longitudinally-extending heat seal adjacent each side of the margins, the strip and overlapping longitudinal margins being joined by a plurality of longitudinally-spaced heat seals, the spaced heat seals and overlapping margins defining between them a series of passages providing communication with the interior of the bag for ingress and egress of the sterilizing vapor, the strip being impermeable to bacteria but highly permeable, in comparison to the tube, to the sterilizing vapor, a transverse heat seal adjacent at least one of the transverse ends of the bag uniting the membrane and the tube and closing said at least one end of the bag, the longitudinally-shaped heat seals carrying stresses produced by the weight of the material received by the bag and relieving the strip and the heat joining the strip and the tube of such stresses.

21. A bag, as defined in claim 20, in which each of the plurality of longitudinally-spaced heat seals has a generally rectangular configuration with the longer side thereof extending along the longitudinal direction of the bag.

22. A bag, as defined in claim 20, in which each of the plurality of longitudinally-spaced heat seals has a generally rectangular configuration with the longer side thereof extending transverse to the longitudinal direction of the bag.

23. A bag, as defined in claim 20, in which each of the plurality of longitudinally-spaced seals has a generally square configuration.

24. A bag, as defined in claim 20, in which the plurality of heat seals includes at least two rows of longitudinally-spaced, V-shaped heat seals, the heat seals of adjacent rows being nested to define labyrinthine passages to impede the entry of bacteria into the interior of the bag.

25. A bag, as defined in claim 20, in which the plurality of heat seals extend in directions that are angularly oriented with respect to the longitudinal and transverse directions of the bag.

26. A bag, as defined in claim 25, in which the heat seals are alternately long and short.

27. A bag, as defined in claim 20, in which the longitudinal margins have a plurality of longitudinally-spaced notches defining tabs, the tabs along one of the margins being heated sealed to the tabs along the other margin, the notches defining the passages.

28. A bag, as defined in claim 20, in which the longitudinal margins are joined by a continuous heat seal extending from the closed end of thhe bag a distance substantially less than half the overall length of the bag.

* * * * *

UNITED STATES PATENT AND TRADEMARK OFFICE
CERTIFICATE OF CORRECTION

PATENT NO. : 4,057,144
DATED : November 8, 1977
INVENTOR(S) : Samuel J. Schuster It is certified that error appears in the above-identified patent and that said Letters Patent are hereby corrected as shown below:

Column 12, line 54, after "products" change the comma (",") to a period (--.--). Column 4, line 51, after "33a" change the comma (",") to a period (--.--). Column 6, line 17, "31d'" should read --32d'--; line 27, "tin" should read --in--. Column 7, line 5, "FIG." should read --FIGS.--; line 45, "former" should read --formed--. Column 8, line 3, "the" (first occurrence) should read --with--. Column 9, line 62, "4" should read --11--. Column 10, line 4, "bacteria-inpermeable" should read --bacteria-impermeable--; line 6, "lingitudinal" should read --longitudinal--; line 7, delete "direction and overlapping longi"; line 8, delete "tudinal"; line 27, "longitudinally spaced" should read --longitudinally-spaced--; line 57, after "heat" and before "joining" insert --seals--. Column 9, line 62, "4" should read --11--.

Signed and Sealed this

Ninth Day of May 1978

[SEAL]

Attest:

RUTH C. MASON
Attesting Officer

LUTRELLE F. PARKER
Acting Commissioner of Patents and Trademarks